United States Patent [19]
Pillay

[11] Patent Number: 6,110,950
[45] Date of Patent: Aug. 29, 2000

[54] MICROBICIDAL COMPOSITIONS AND METHODS USING SYNERGISTIC COMBINATIONS OF PROPICONAZOLE AND 2-MERCAPTOBENZOTHIAZOLE

[75] Inventor: Allan Saroj Pillay, Shallcross, South Africa

[73] Assignee: Buckman Laboratories International Inc., Memphis, Tenn.

[21] Appl. No.: 09/263,524

[22] Filed: Mar. 5, 1999

Related U.S. Application Data

[60] Provisional application No. 60/076,909, Mar. 5, 1998.
[51] Int. Cl.[7] .............................. A01N 43/64; A01N 43/78
[52] U.S. Cl. ............................................. 514/367; 514/383
[58] Field of Search ..................................... 514/367, 383

[56] References Cited

U.S. PATENT DOCUMENTS 5,880,143  3/1999  Goettsche et al. ...................... 514/383

FOREIGN PATENT DOCUMENTS

| | | |
|---|---|---|
| 0 393 746 | 10/1990 | European Pat. Off. . |
| 0 741 969 A2 | 11/1996 | European Pat. Off. . |
| 2 025 769 | 1/1980 | United Kingdom . |
| WO 96/01054 | 1/1996 | WIPO . |
| WO 96/15885 | 5/1996 | WIPO . |
| WO 97/39865 | 10/1997 | WIPO . |
| WO 98/42190 | 10/1998 | WIPO . |

*Primary Examiner*—Allen J. Robinson
*Attorney, Agent, or Firm*—Morgan, Lewis & Bockius LLP

[57] ABSTRACT

Microbicidal compositions containing synergistic combinations of propiconazole, (RS)-1-2-[(2,4-dichlorophenyl)-2-propyl-1,3-dioxalan-2ylmethyl]-1H-1,2,4-triazole, and 2-mercaptobenzothiazole or alkali metal salt thereof are described. The propiconazole and 2-mercaptobenzothiazole or an alkali metal salt thereof are applied to a substrate or aqueous system subject to the growth of at least one microorganism. Methods for controlling the growth of microorganisms on various substrates and in various aqueous systems are also described. The combination of propiconazole and 2-mercaptobenzothiazole or an alkali metal salt thereof is particularly useful as microbicidal in the leather industry, the lumber industry, the papermaking industry, the textile industry, the agricultural industry, and the coating industry, as well as in industrial process waters.

11 Claims, No Drawings

MICROBICIDAL COMPOSITIONS AND METHODS USING SYNERGISTIC COMBINATIONS OF PROPICONAZOLE AND 2-MERCAPTOBENZOTHIAZOLE

This application claims benefit of copending U.S. Provisional Application No. 60/076,909 filed on Mar. 5, 1998.

FIELD OF THE INVENTION

The present invention relates to compositions and methods for controlling the growth of microorganisms on a variety of substrates and in aqueous systems. More particularly, the invention relates to a synergistic combination of propiconazole, also known as (RS)-1-2-[(2,4-dichlorophenyl)-4-propyl-1,3-dioxalan-2-ylmethyl]-1H-1,2,4-triazole, and 2-mercaptobenzothiazole or an alkali metal salt thereof.

BACKGROUND OF THE INVENTION

A large variety of commercial, industrial, agricultural, and wood materials or products are subject to microbiological attack or degradation which reduces or destroys their economic value. Examples of such materials or products include surface coatings, lumber, seeds, plants, leather and plastics. The various temperatures at which such materials or products are manufactured, stored, or used as well as their intrinsic characteristics make them susceptible to growth, attack, and degradation by common microorganisms such as algae, fungi, yeasts, and bacteria. These microorganisms may be introduced during a manufacturing or other industrial process, by exposure to air, tanks, pipes, equipment, and humans. They can also be introduced while using a material or product, for example, by multiple openings and reclosures of packages or from stirring or removing material with contaminated objects.

Aqueous systems are also highly subject to microbiological growth, attack, and degradation. These aqueous systems may be fresh, brackish or saltwater systems. Exemplary aqueous systems include, but are not limited to, latexes, surfactants, dispersants, stabilizers, thickeners, adhesives, starches, waxes, proteins, emulsifying agents, cellulose products, metal working fluids, cooling water, waste water, aqueous emulsions, aqueous detergents, coating compositions, paint compositions, and resins formulated in aqueous solutions, emulsions or suspensions. These systems frequently contain relatively large amounts of water and organic material causing them to be environments well-suited for microbiological growth and thus attack and degradation.

Microbiological degradation of aqueous systems may manifest itself as a variety of problems, such as loss of viscosity, gas formation, objectionable odors, decreased pH, emulsion breaking, color change, and gelling. Additionally, microbiological deterioration of aqueous systems can cause fouling of the related water-handling system, which may include cooling towers, pumps, heat exchangers, and pipelines, heating systems, scrubbing systems, and other similar systems.

Another objectionable phenomenon occurring in aqueous systems, particularly in aqueous industrial process fluids, is slime formation. Slime formation can occur in fresh, brackish or salt water systems. Slime consists of matted deposits of microorganisms, fibers and debris. It may be stringy, pasty, rubbery, tapioca-like, or hard, and may have a characteristic undesirable odor that is different from that of the aqueous system in which it formed. The microorganisms involved in its formation are primarily different species of spore-forming and non-spore-forming bacteria, particularly capsulated forms of bacteria which secrete gelatinous substances that envelop or encase the cells. Slime microorganisms also include filamentous bacteria, filamentous fungi of the mold type, yeast, and yeast-like organisms. Slime reduces yields in production and causes plugging, bulking, and other problems in industrial water systems.

Various chemicals known as microbicide have been used to prevent microbiological deterioration of industrial systems, raw materials, and products. Despite the existence of such microbicide, industry is constantly seeking more cost-effective technology which offers equal or better protection at lower cost and lower concentration. The concentration of conventional microbicide and the corresponding treatment costs for such use, can be relatively high. Important factors in the search for cost-effective microbicide include the duration of microbicidal effect, the ease of use and the effectiveness of the microbicide per unit weight.

SUMMARY OF THE INVENTION

In view of industry's search for more cost effective microbicide, the invention offers an improvement over current products or practices.

One embodiment of the invention provides a microbicidal composition. The composition contains propiconazole and 2-mercaptobenzothiazole (2-MBT) or an alkali metal salt thereof. In the composition, propiconazole and the 2-MBT are present in a combined amount synergistically effective to control the growth of at least one microorganism.

Another embodiment of the invention provides a method for controlling the growth of a microorganism on a substrate. This method contacts a substrate susceptible to the growth of microorganisms with propiconazole and 2-MBT. The propiconazole and the 2-MBT are present in a combined amount synergistically effective to control the growth of at least one microorganism on the substrate.

Another embodiment of the invention provides a method for controlling the growth of microorganisms in an aqueous system capable of supporting growth of a microorganism. This method treats the aqueous system with propiconazole and 2-MBT. Propiconazole and 2-MBT are present in a combined amount synergistically effective to control the growth of at least one microorganism in the aqueous system.

The synergistic combination of propiconazole and 2-MBT, according to the invention is useful in preventing the microbiological attack, degradation, or deterioration of various types of raw materials and products such as leather, textiles, pulp, paper and paperboard, coatings, lumber, as well as agricultural products such as seeds and crops. Advantageously, the synergistic combination may be used in various industrial processes used to prepare or manufacture these products. Accordingly, additional embodiments of the invention employ the combination to control the growth of microorganisms on or in such industrial products, raw materials or processes.

The foregoing and other features and advantages of the invention will be made more apparent from the following detailed description and preferred embodiments.

DETAILED DESCRIPTION OF THE INVENTION

When two chemical microbiocides are used in combination, either in a single composition or as two separate additions at the point of use, three results are possible: 1) an additive (neutral) effect; 2) an antagonistic effect; or 3) a synergistic effect. An additive (neutral) effect has no economic advantage over the individual microbiocides. An antagonistic effect would produce a negative result. Only synergism, which is much less likely than an additive or an antagonistic effect, gives a positive result and, therefore possesses economic advantages. According to the invention, the combination of propiconazole and 2-mercaptobenzothiazole (2-MBT) or an alkali metal salt thereof demonstrates an unexpected, synergistic microbicidal effect. The combination of propiconazole and 2-MBT, therefore, achieves superior microbicidal activity at lower propiconazole and 2-MBT concentrations as compared to the microbicidal capability of propiconazole or 2-MBT alone. Such a superior effect presents a distinct economic advantage and increases propiconazole's effectiveness per unit weight.

In one embodiment, the invention relates to a microbicidal composition comprising propiconazole and 2-MBT. Propiconazole and 2-MBT are present in a combined amount synergistically effective to control the growth of at least one microorganism.

Propiconazole, (RS)-1-2-[(2,4-dichlorophenyl)-4-propyl-1,3-dioxalan-2-ylmethyl]-1H-1,2,4-triazole, is a known fungicide (U.S. Pat. Nos. 5,627,188, 5,567,705, 5,403,844, 5,326,777, 5,250,559 and 5,200,421). Propiconazole has the following chemical structure:

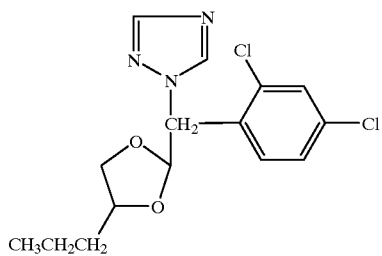

Propiconazole is available under the BUSAN® 1292 tradename from Buckman Laboratories Inc., Memphis, Tenn. and under the WOCASEN 250EC tradename from Janssen Pharmaceutica, Titusville, N.J. BUSAN® 1292 is a formulation containing 23.6% propiconazole and 75% inert ingredients including a nonylphenol ethyleneoxide/polyethylene oxide surfactant.

2-mercaptobenzothiazole and the alkali metal salts thereof have microbiocidal activity and have the following chemical structure:

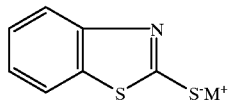

wherein M is hydrogen or an alkali metal. Preferably, M is sodium or potassium. In the context of the invention, the term "2-MBT" refers to 2-mercaptobenzothiazole and the alkali metal salts thereof. Sodium 2-mercaptobenzothiazole is available under the BUSAN® 1214 tradename from Buckman Laboratories Inc., Memphis, Tenn. BUSAN® 1214 is a 50% aqueous formulation of sodium 2-mercaptobenzothiazole.

Depending on the application, microbicidal compositions according to the invention may be prepared in various forms known in the art. For example, the composition may be prepared in liquid form as an aqueous solution, dispersion, emulsion, or suspension, a dispersion or suspension in a non-solvent, or as a solution by dissolving propiconazole and 2-MBT in a solvent or combination of solvents. Suitable solvents include, but are not limited to, methyl ethers of glycols, M-pyrol or 1-methyl-pyrrolidinone, or petroleum distillates. The microbicidal composition may be prepared as a concentrate for dilution prior to its intended use. Common additives such as surfactants, emulsifiers, dispersants, and the like may be used as known in the art to increase the solubility of propiconazole or 2-MBT in a liquid composition or system, such as an aqueous composition or system. In many cases, the microbicidal composition of the invention may be prepared by mixing liquid formulations of propiconazole and 2-MBT by simple agitation.

Microbicidal compositions of the invention may also be prepared in solid form, for example as a powder or tablet, using means known in the art. For example, a liquid product containing propiconazole or 2-MBT is deposited on carriers such as diatomaceous earth or kaolin. The resulting solid or solids may be mixed together or one solid may be mixed with the other component, or a solution or liquid formulation containing the component, to form a powder or tablet.

The propiconazole and 2-MBT may be combined in a single composition. Alternatively, the propiconazole and 2-MBT may be employed as separate components such that combined amount for the intended use is effective to control the growth of at least one microorganism.

As discussed above, the combination of propiconazole and 2-MBT possesses a synergistic microbicidal effect to control the growth of at least one microorganism as compared to the microbicidal capability of the propiconazole or 2-MBT alone. According to the invention, control of the growth of a microorganism on a substrate or in an aqueous system means control to, at, or below a desired level and for a desired period of time for the particular substrate or system. This can vary from the complete prevention or inhibition of microbiological growth to control at a certain desired level and for a desired time. The synergistic combination of propiconazole and 2-MBT described here can, in many cases, reduce the total microbiological count to undetectable limits and maintain the count at that level for a significant period of time. Accordingly, the combination may be used to preserve a substrate or system.

The effective amount or percentage of the synergistic combination of propiconazole and 2-MBT necessary to achieve the desired result will vary somewhat depending on the substrate or aqueous system to be protected, the conditions for microbial growth, the particular microbicide, and the degree of protection desired. For a particular application, the amount of choice may be determined by routine testing of various amounts prior to treatment of the entire affected substrate or system. In general, an effective amount used on a substrate ranges from about 0.0001% to about 4% (w/w); preferably about 0.0001% to about 1.0%. With aqueous systems, an effective amount may range from about 0.5 to about 10,000 parts per million, more preferably from about 5 to about 5000 parts per million of the aqueous system, and most preferably from, about 10 to about 1000 parts per million. Similar amounts effectively control slime formation. For slime control, effective amounts preferably range from about 1 to about 1000 parts per million, and more preferably, from about 1 to about 200 parts per million of the aqueous system.

In a preferred embodiment, combinations of propiconazole and 2-MBT are those synergistic combinations where the weight ratio of propiconazole to 2-MBT range from about 99:1 to about 1:99. More preferably the weight ratio is from about 60:10 to about 10:60, and most preferably, from about 50:50 to about 25:75. The weight ratio may vary depending on the microbicide, the intended use, the microorganism encountered as well as the particular material, product, or system to which the combination according to the invention is applied.

The synergistic combination of propiconazole and 2-MBT may be applied in a variety of industrial uses and processes for microorganism control. The combination may be used in place of and in the same manner as other microbiocides traditionally used in the particular industry. As discussed above, such industries include, but are not limited to the leather industry, the lumber industry, the papermaking industry, the textile industry, the agricultural industry, and the coating industry. The combination of propiconazole and 2-MBT may also be used with aqueous systems such as those previously discussed which are subject to microbiological attack and degradation. The problems caused by microbiological attack and deterioration in these various applications has been described above. The use of a synergistic combination of propiconazole and 2-MBT according to the invention to control the growth of microorganisms in particular exemplary applications is described below.

The invention also relates to a method for controlling the growth of microorganisms on various substrates. The method comprises the step of contacting a substrate susceptible to microbiological growth or attack with propiconazole and 2-MBT, as described above. Propiconazole and 2-MBT are present in a combined amount effective to control the growth of at least one microorganism on the substrate. Preferably, the method may be used to eliminate or prevent substantially all microbiological growth on the substrate. As discussed above, propiconazole and 2-MBT may be applied together or as separate compositions. Preferred applications of this general method are discussed below.

In the leather industry, the combination of propiconazole and 2-MBT may be used to control the growth of microorganisms on a hide during a tanning process. To achieve this control, the hide is contacted with a combined amount of propiconazole and 2-MBT effective to control the growth of at least one microorganism on the hide. The synergistic combination of propiconazole and 2-MBT may be used in the tanning process in similar amounts and manner similar to that used to apply other microbiocides used in the tanning industry. The type of hide may be any type of hide or skin that is tanned, for example cowhide, snake skin, alligator skin, sheep skin, and the like. The amount used, to some extent, will depend on the degree of microbiological resistance required and may be readily determined by one skilled in the art.

A typical tanning process comprises a number of stages, including, but not limited to, a pickling stage, a chrome-tanning stage, a vegetable-tanning stage, a post-tan washing stage, a retanning stage, a dyeing stage, and a fat liquoring stage. The combination of propiconazole and 2-MBT may be used during all process stages in the tanning process in addition to those stages where a known microbiological problem is occurring. In each stage, the combination of propiconazole and 2-MBT may be a component of the appropriate tanning liquor applied to the hide undergoing tanning.

Incorporating propiconazole and 2-MBT in a tanning liquor protects the hide from microbiological deterioration during the tanning process. Preferably, the combination is uniformly dispersed, e.g., under agitation, into an appropriate liquor to be used in a tanning process. Typical tanning liquors include, for example, a pickling liquor, a chrome-tanning liquor, a vegetable-tanning liquor, a post-tan washing liquor, a retanning liquor, a dye liquor, and a fatliquor. This method of application ensures that the combination applied to the hides protects against microbiological attack, deterioration, or other microbiological degradation.

In a somewhat analogous nature, the combination of the invention may also be employed to control the growth of microorganisms on a textile substrate in a textile manufacturing process. Contacting the textile substrate with a synergistic combination of propiconazole and 2-MBT according to the invention effectively controls the growth of a microorganism on the textile substrate. In a textile process, the combination may be used in similar amounts and a manner similar to other antimicrobial compounds commonly used in such processes. As one of ordinary skill would appreciate, particular amounts generally depend on the textile substrate and the degree of microbiological resistance required.

The step of contacting the textile substrate with the combination of propiconazole and 2-MBT may be accomplished using means known in the textile art. To control microbiological growth, a textile process generally dips the textile substrate into a bath containing a microbicide alone or with other chemicals used to treat the textile substrate. Alternatively, the textile substrate may be sprayed with a formulation containing a microbicide. In the bath or the spray, the combination of propiconazole and 2-MBT according to the invention are present in a combined amount synergistically effective to control the growth of at least one microorganism on the textile substrate. Preferably, the bath and the spray are aqueous-based compositions.

To preserve the value of its raw materials and products, the lumber industry also must control the growth of microorganisms in order to prevent microbiological degradation of lumber. The synergistic combination of propiconazole and 2-MBT according to the invention is effective to control the growth of microorganisms on lumber. Synergistic combinations of propiconazole and 2-MBT may be used to protect the lumber in similar amounts and a similar manner employed for other microbiocides used in the lumber industry. Contacting lumber with an effective amount of the combination may be accomplished, for example, by spraying the lumber with an aqueous formulation containing the synergistic combination of propiconazole and 2-MBT by dipping the lumber into a dip bath containing the combination, or other means known in the art. Dipping the lumber in an aqueous bath is preferred.

Propiconazole and 2-MBT are preferably uniformly dispersed in a bath (for example, by agitation) prior to the dipping of the lumber into the bath. In general, the lumber is dipped into the bath, raised, allowed to drip dry, and then air dried. The dip time will depend, as is known in the art, on a variety of factors such as the microbicide, the degree of microbiological resistance desired, the moisture content of the lumber, type and density of the wood, etc. Pressure may be applied to promote penetration of the combination into the lumber being treated. Applying a vacuum to the upper surface of the lumber may also be used to degas the lumber and promote increased wetting of the lumber by a bath containing the microbicidal combination.

The synergistic combination of propiconazole and 2-MBT according to the invention also has uses in the agricultural industry. To control the growth of microorganisms on a seed or plant, the seed or plant may be contacted with propiconazole and 2-MBT in a combined amount synergistically effective to control the growth of at least one microorganism on the seed or plant. This contacting step may be accomplished using means and amounts known in the agricultural industry for other microbiocides. For example, the seed or plant may be sprayed with an aqueous formulation containing the combination of propiconazole and 2-MBT or dipped into a bath containing the combination. After being sprayed or dipped, the seed or plant is generally dried by means known in the art such as drip drying, heated drying, or air drying. For plants or crops, the combination may also be applied using a soil drench. Soil drenching is particularly advantageous when the microorganisms of concern inhabit the soil surrounding the plant.

Yet another aspect of the invention is a method for controlling the growth of microorganisms in an aqueous system capable of supporting such growth. The aqueous system is treated with propiconazole and 2-MBT such that the propiconazole and 2-MBT are present in a combined amount synergistically effective to control the growth of at least one microorganism in the aqueous system. This includes controlling, and preferably preventing, slime formation in the aqueous system.

Examples of various aqueous systems include, but are not limited to, latexes, surfactants, dispersants, stabilizers, thickeners, adhesives, starches, waxes, proteins, emulsifying agents, cellulose products, aqueous emulsions, aqueous detergents, coating compositions, paint compositions, alum compositions, and resins formulated in aqueous solutions, emulsions or suspensions. The combination may also be employed in aqueous systems used in industrial processes such as metal working fluids, cooling waters (both intake cooling water and effluent cooling water), and waste waters including waste waters or sanitation waters undergoing treatment of the waste in the water, e.g. sewage treatment.

As with the other uses discussed above, the synergistic combination of the invention may be used in the same amounts and in the same manner as microbiocides traditionally used in these various aqueous systems. The combination not only protects the aqueous system prior to use or when stored, but in many cases protects the aqueous system when in use or in appropriate applications even after the aqueous system has dried. When used in a paint formulation for example, the combination not only protects the paint in the can, but also the paint film after being applied to a substrate.

Another embodiment of the invention is a method for controlling the growth of microorganisms on paper or in a papermaking process, e.g., in a pulp or paper slurry and on a finished paper product such as paper board. The paper, pulp, or slurry is contacted with propiconazole and 2-MBT in a combined amount synergistically effective to control the growth of at least one microorganism on the paper, the pulp or in a slurry. The contacting step is accomplished using means and amounts known in the papermaking art.

According to this aspect of the invention, for example, a forming web on a papermaking machine (or a wet-lap pulp) may be contacted with the synergistic combination of propiconazole and 2-MBT by spraying an aqueous dispersion containing the propiconazole and 2-MBT onto the pulp after the pulp leaves the presses in a papermaking process. Or, the propiconazole and 2-MBT may be incorporated into a bath used at the wet or size press and the web contacted by nipping the web to incorporate the combination into the web with any other agents applied at the press. Alternatively, the pulp may be contacted by mixing the propiconazole and 2-MBT into the pulp/white water mixture, preferably prior to the pulp reaching the formation wire.

When treating paper (which includes paperboard and other cellulosic products or substrates), the propiconazole and 2-MBT may be added into pulp slurries in the headbox, in the substrate forming solution, or in the white water system to treat the water system itself or for incorporation into the body of the paper. Alternatively, as with other known microbiocides, the synergistic combination of propiconazole and 2-MBT according to the invention may be mixed into a coating used to coat the finished paper.

The synergistic microbicidal activity of combinations of propiconazole and 2-MBT, described above, has been confirmed using standard laboratory techniques as discussed below. The following examples are intended to illustrate, not limit, the invention.

EXAMPLES

Example 1

Application of Combinations of Propiconazole and Sodium 2-MBT in the Treatment of Leather Several dilutions of formulations containing both propiconazole and sodium 2-MBT were investigated with respect to their ability to prevent the formation of fungi, mold and yeast in leather.

The following formulations were used to treat the leather:

Formulation A: 95% BUSAN ® 1214 and 5% BUSAN ® 1292
Formulation B: 90% BUSAN ® 1214 and 10% BUSAN ® 1292

BUSAN® 1214 is a 50% aqueous formulation of sodium 2-MBT and is commercially available from Buckman Laboratories Inc., Memphis, Tenn. BUSAN® 1292 is a formulation containing 23.6% propiconazole and 75% inert ingredients including a nonylphenol ethyleneoxide/polyethylene oxide surfactant and is also commercially available from Buckman Laboratories Inc., Memphis, Tenn.

Treatment Method

Pre-pickled hides were placed in a drum to which was then added water having a temperature of 78–82° F. and 6% sodium chloride (NaCl). The drum was started and allowed to run for 15 minutes. Next 0.3% formic acid diluted 1:10 in water was added to the drum which was then run for 30 minutes. Afterwards, 0.8% sulfuric acid diluted 1:15 in water was added to the drum. After running the drum for 2.5 hours, the drum was stopped and the pH of the float was taken and found to range from about 1.8 to about 2.2. The color of the cut of the leather was also checked with Bromocresol Green dye which ideally was yellow to very light green. Next a solution of 3% CHROMOSAL B (available from Bayer Co. containing 25% $Cr_2O_3$ and having 33% basicity) was added to the drum. Once the drum was started, the propiconazole and Na 2-MBT combination was added. After 3 hours, 5% BAYCHROME A (available from Bayer Co. containing 23% $Cr_2O_3$ and having 66% basicity) was added to the drum which was then allowed to run overnight. Next the chrome penetration in the hides was evaluated visually. If chrome penetration was not sufficient, the drum was allowed to run for a longer period of time until sufficient chrome penetration was achieved. Once achieved, a basification process was begun by very slowly adding a solution of 1.7% sodium bicarbonate to the drum of which the heaters were turned on to increase the temperature within the drum. The sodium bicarbonate addition was added at such a rate as to not be completed under an hour. After sodium bicarbonate addition was complete, the drum was then run for 4 hours. After 4 hours, the pH of the float was checked. If the pH was between 3.65 and 3.85, the float was drained and the leather was washed with cold water. If the pH was lower than 3.65, additional sodium bicarbonate was added and the drum was run for another hour. The pH was again tested. If the pH was still too low, the process of adding sodium bicarbonate and running the drum was repeated until the pH fell within the desired range.

Evaluation Method

Once a week for four weeks, leather samples treated with aqueous dilutions of formulations comprising a combination of propiconazole and sodium 2-MBT as described above, were evaluated for growth of fungi, mold and yeast. The leather samples of varying thickness were evaluated for growth of fungi, mold and yeast according to ASTM D-3273-73T by using a tropical chamber. The tropical chamber is an enclosed unit containing a nutrient rich medium under high humidity conditions which is inoculated with a variety of fungi, mold and yeast growth and accelerates the activity of these organisms. Evaluations were made for the grain surface of the leather samples based on percent growth. The results are shown in Table 1.

TABLE 1

| Sample No. | Formulation | Leather Sample thickness (mm) | % growth/week no. |
|---|---|---|---|
| 1 | 0.1% A | 1 | 0/1 |
|   |        |   | 0/2 |
|   |        |   | 0/3 |
|   |        |   | 0/4 |
| 2 | 0.1% A | 2 | 0/1 |
|   |        |   | 0/2 |
|   |        |   | 0/3 |
|   |        |   | 0/4 |
| 3 | 0.15% B | 4 | 0/1 |
|   |         |   | 0/2 |
|   |         |   | 0/3 |
|   |         |   | 0/4 |
| 4 | 0.15% B | 5 | 0/1 |
|   |         |   | 0/2 |
|   |         |   | 10/3 |
|   |         |   | 30/4 |

Example 2

Application of Various Treatment Solutions to Leather Samples

Leather samples were treated according to the method described in Example 1, with the following formulations:

Formulation C: Prosan ® 24
Formulation D: 95% Na 2-MBT and 5% BUSAN ® 1292
Formulation E: 90% Na 2-MBT and 10% BUSAN ® 1292
Formulation F: 50% aqueous Na 2-MBT
Formulation G: BUSAN ® 1292

Prosan®24 is a formulation containing 25% propiconazole and 75% inert ingredients. It is commercially available from Janssen Pharmaceutica, Titusville, N.J.

Once a week for 9 weeks, leather samples treated with the solutions described above were evaluated for growth of fungi, mold and yeast in a tropical chamber as described in Example 1. Evaluations were made for both the grain and the flesh surface of the leather samples based on percent growth. The results are shown in Table 2.

TABLE 2

EVALUATION DATA IN TROPICAL CHAMBER
EXPERIMENTAL PRODUCT: Propiconazole and Na 2-MBT

| DATA: GRAIN (G)/FLESH (F) SURFACE ACTIVE AGENT | DOSAGE % | 1 WEEK G/F | 2 WEEK G/F | 3 WEEK G/F | 4 WEEK G/F | 5 WEEK G/F | 6 WEEK G/F | 7 WEEK G/F | 8 WEEK G/F | 9 WEEK G/F |
|---|---|---|---|---|---|---|---|---|---|---|
| Control (no treatment) | 0 | 10/10 | 2/4 | 0 | 0 | 0 | 0 | 0 | 0 | 0 |
| C | 0.05% | 10/10 | 10/10 | 10/10 | 9/9 | 7/8 | 5/5 | 5/4 | 2/0 | 0 |
| C | 0.10% | 10/10 | 10/10 | 10/10 | 9/9 | 8/5 | 7/2 | 5/2 | 5/2 | 0 |
| C | 0.14% | 10/10 | 10/10 | 10/10 | 10/10 | 10/10 | 9/10 | 9/9 | 8/9 | 8/8 |
| D | 0.08% | 10/10 | 10/10 | 10/10 | 10/10 | 10/10 | 10/10 | 10/10 | 10/10 | 10/10 |
| E | 0.08% | 10/10 | 10/10 | 9/9 | 8/9 | 8/9 | 8/8 | 8/8 | 8/7 | 8/7 |
| F | 0.08% | 10/10 | 10/10 | 10/10 | 10/10 | 10/10 | 10/10 | 10/10 | 10/10 | 10/9 |
| G | 0.08% | 10/10 | 10/10 | 10/10 | 10/10 | 10/10 | 10/9 | 9/9 | 9/9 | 9/9 |

Key for the values on the evaluation

| | |
|---|---|
| 10 | No Growth |
| 9 | |
| 8 | Slight Growth |
| 7 | |
| 6 | Medium Growth |
| 5 | |
| 4 | Moderately/Heavy Growth |
| 3 | |
| 2 | Heavy Growth |
| 1 | |
| 0 | Completely Covered |

Example 3

Application of Combinations of Propiconazole and Sodium 2-MBT and Leatherguard 301 in the Treatment of Leather Hides of varying thicknesses were treated with a combination of propiconazole and sodium 2-MBT and compared to similar hides treated with a commercial formulation known as Leatherguard 301. The treated hides were evaluated for their ability to prevent the formation of fungi, mold and yeast in the hide. The following formulations were used to treat the leather:

Formulation H: BUSAN ® 1112
Formulation J: Leatherguard 301

BUSAN® 1112 is an aqueous formulation comprised of 96% by weight sodium 2-MBT and 4% by weight BUSAN® 1292, and is commercially available from Buckman Laboratories Inc., Memphis, Tenn. BUSAN® 1292 is a formulation containing 23.6% propiconazole and 75% inert ingredients including a nonylphenol ethyleneoxide/polyethylene oxide surfactant and is also commercially available from Buckman Laboratories Inc., Memphis, Tenn.

Leatherguard 301 is a 25–30% by weight 2-(Thiocyanomethylthio)-benzothiazole (TCMTB) based product which is commercially available from South African Paper Co., Ltd. (SAPCo) located in Parkland, South Africa.

Treatment Method

Pre-pickled hides were placed in a drum to which was then added an aqueous salt solution. The drum was started and allowed to run for a time sufficient to allow for complete hide hydration. Next, acid was added to adjust the pH and the drum was run for a time sufficient to achieve a pH in the range of about 1.5–2.5. Next, a chrome solution was added to the drum. Once the drum was started, the treating solution, i.e, BUSAN® 1112 or Leatherguard 301 was added. After a time sufficient to allow the treating solution to fully penetrate the hide, a chrome solution was added to the drum and the drum was allowed to run for a time sufficient to allow the chrome to penetrate the hide. Next the chrome penetration in the hides was evaluated visually. If chrome penetration was not sufficient, the drum was allowed to run for a longer period of time until sufficient chrome penetration was achieved. Once achieved, base was added and the drum was run for a time sufficient to achieve a float pH of between 3–5. At this time the float was drained and the leather was washed.

Evaluation Method

Once a week for four weeks, the treated leather samples were evaluated for growth of fungi, mold and yeast in a tropical chamber as described in Example 1. Evaluations were made for the grain surface of the leather samples based on percent growth. The results are shown in Tables 3, 4 and 5.

TABLE 3

| SAMPLE | TREATMENT | WEEK NO. | % GROWTH 0 | 10 | 20 | 30 | 40 | 50 | 60 | 70 | 80 | 90 | 100 |
|---|---|---|---|---|---|---|---|---|---|---|---|---|---|
| Hide 1 - neck 3.5 mm thick | 0.1% H | 1 | | | | | | | | | | | |
| | | 2 | | | | | | | | | | | |
| | | 3 | | | | | | | | | | | |
| | | 4 | | | | | | | | | | | |
| Hide 1 - neck 3 mm thick | 0.1% J | 1 | | | | | | | | | | | |
| | | 2 | | | | | | | | | | | |
| | | 3 | | | | | | | | | | | |
| | | 4 | | | | | | | | | | | |
| Hide 1 - butt 3 mm thick | 0.1% H | 1 | | | | | | | | | | | |
| | | 2 | | | | | | | | | | | |
| | | 3 | | | | | | | | | | | |
| | | 4 | | | | | | | | | | | |
| Hide 1 - butt 3.5 mm thick | 0.1% J | 1 | | | | | | | | | | | |
| | | 2 | | | | | | | | | | | |
| | | 3 | | | | | | | | | | | |
| | | 4 | | | | | | | | | | | |

TABLE 4

| SAMPLE DESCRIPTION | TREATMENT | WEEK NO. | % GROWTH 0 | 10 | 20 | 30 | 40 | 50 | 60 | 70 | 80 | 90 | 100 |
|---|---|---|---|---|---|---|---|---|---|---|---|---|---|
| Hide 2 - neck 3 mm thick | 0.1% H | 1 | | | | | | | | | | | |
| | | 2 | | | | | | | | | | | |
| | | 3 | | | | | | | | | | | |
| | | 4 | | | | | | | | | | | |
| Hide 2 - neck 4 mm thick | 0.1% J | 1 | | | | | | | | | | | |
| | | 2 | | | | | | | | | | | |
| | | 3 | | | | | | | | | | | |
| | | 4 | | | | | | | | | | | |
| Hide 2 - butt 3 mm thick | 0.1% H | 1 | | | | | | | | | | | |
| | | 2 | | | | | | | | | | | |
| | | 3 | | | | | | | | | | | |
| | | 4 | | | | | | | | | | | |
| Hide 2 - butt 3 mm thick | 0.1% J | 1 | | | | | | | | | | | |
| | | 2 | | | | | | | | | | | |
| | | 3 | | | | | | | | | | | |
| | | 4 | | | | | | | | | | | |

TABLE 5

| SAMPLE DESCRIPTION | TREATMENT | WEEK NO. | % GROWTH 0 | 10 | 20 | 30 | 40 | 50 | 60 | 70 | 80 | 90 | 100 |
|---|---|---|---|---|---|---|---|---|---|---|---|---|---|
| Hide 3 - neck 3 mm thick | 0.1% H | 1 | | | | | | | | | | | |
| | | 2 | | | | | | | | | | | |
| | | 3 | | | | | | | | | | | |
| | | 4 | | | | | | | | | | | |

TABLE 5-continued

| SAMPLE DESCRIPTION | TREATMENT | WEEK NO. | % GROWTH 0 10 20 30 40 50 60 70 80 90 100 |
|---|---|---|---|
| Hide 3 - neck 3 mm thick | 0.1% J | 1 | |
| | | 2 | |
| | | 3 | |
| | | 4 | |
| Hide 3 - butt 3 mm thick | 0.1% H | 1 | |
| | | 2 | |
| | | 3 | |
| | | 4 | |
| Hide 3 - butt 3 mm thick | 0.1% J | 1 | |
| | | 2 | |
| | | 3 | |
| | | 4 | |

The claimed invention is:

1. A microbicidal composition comprising:
propiconazole and 2-mercaptobenzothiazole or an alkali metal salt thereof, wherein the propiconazole and the 2-mercaptobenzothiazole or an alkali metal salt thereof are present in a combined amount synergistically effective to control the growth of at least one microorganism.

2. A microbicidal composition according to claim 1, wherein the microorganism is selected from algae, fungi, mold, and bacteria.

3. A method for controlling the growth of microorganisms on a substrate comprising the step of contacting a substrate susceptible to the growth of microorganisms with a microbicidal composition comprising propiconazole and 2-mercaptobenzothiazole or an alkali metal salt thereof, wherein the propiconazole and the 2-mercaptobenzothiazole or alkali metal salt thereof are present in a combined amount synergistically effective to control the growth of at least one microorganism on the substrate.

4. A method according to claim 3, wherein the microorganism is selected from algae, fungi, mold, and bacteria.

5. A method according to claim 3, wherein the substrate is a hide, a textile substrate, lumber, a seed, or a plant.

6. A method for controlling the growth of microorganisms in an aqueous system capable of supporting growth of a microorganism comprising the step of treating the aqueous system with propiconazole and 2-mercaptobenzothiazole or an alkali metal salt thereof, wherein the propiconazole and the 2-mercaptobenzothiazole or an alkali metal salt thereof are present in a combined amount synergistically effective to control the growth of at least one microorganism.

7. A method according to claim 6, wherein the microorganism is selected from algae, fungi, mold, and bacteria.

8. A method according to claim 6, wherein said aqueous system is selected from the group consisting of a latex, a metal working fluid, an aqueous emulsion, an aqueous detergent, cooling water, and an aqueous resin formulation.

9. A method for controlling the growth of microorganisms on pulp or paper in a papermaking process, comprising the step of contacting the pulp or paper with propiconazole, and 2-mercaptobenzothiazole or an alkali metal salt thereof, wherein the propiconazole and the 2-mercaptobenzothiazole or an alkali metal salt thereof are present in a combined amount synergistically effective to control the growth of at least one microorganism.

10. A method according to claim 9, wherein the pulp is contacted by mixing the propiconazole and 2-mercaptobenzothiazole or an alkali metal salt thereof into a pulp slurry prior to reaching a formation wire in a papermaking process.

11. A method according to claim 9, wherein the microorganism is selected from algae, fungi, mold, and bacteria.

* * * * *